United States Patent [19]
Dailey et al.

[11] Patent Number: 5,908,612
[45] Date of Patent: *Jun. 1, 1999

[54] ORAL CARE COMPOSITIONS COMPRISING LIQUID POLYOXYALKYLENE COMPOUNDS AS SOLUBILIZERS/GELLING AGENTS

[75] Inventors: James S. Dailey, Grosse Ile; Jay G. Otten, Flat Rock, both of Mich.; Jay Amarasekara, Clifton Park, N.Y.; Sridhar Gopalkrishnan, Woodhaven, Mich.

[73] Assignee: BASF Corporation, Mt. Olive, N.J.

[*] Notice: This patent is subject to a terminal disclaimer.

[21] Appl. No.: 08/775,328

[22] Filed: Dec. 31, 1996

[51] Int. Cl.$^6$ .............................. A61K 7/16; A61K 7/18; A61K 7/22

[52] U.S. Cl. .................. 424/49; 424/52; 424/53

[58] Field of Search .......................... 424/49–58

[56] References Cited

FOREIGN PATENT DOCUMENTS 47-48366 B4  12/1972  Japan .

*Primary Examiner*—Shep K. Rose
*Attorney, Agent, or Firm*—Nixon & Vanderhye P.C.

[57] ABSTRACT

The present invention relates to oral care compositions comprising Liquid Polyoxyalkylene Compounds as Solubilizers/Gelling Agents.

5 Claims, 1 Drawing Sheet

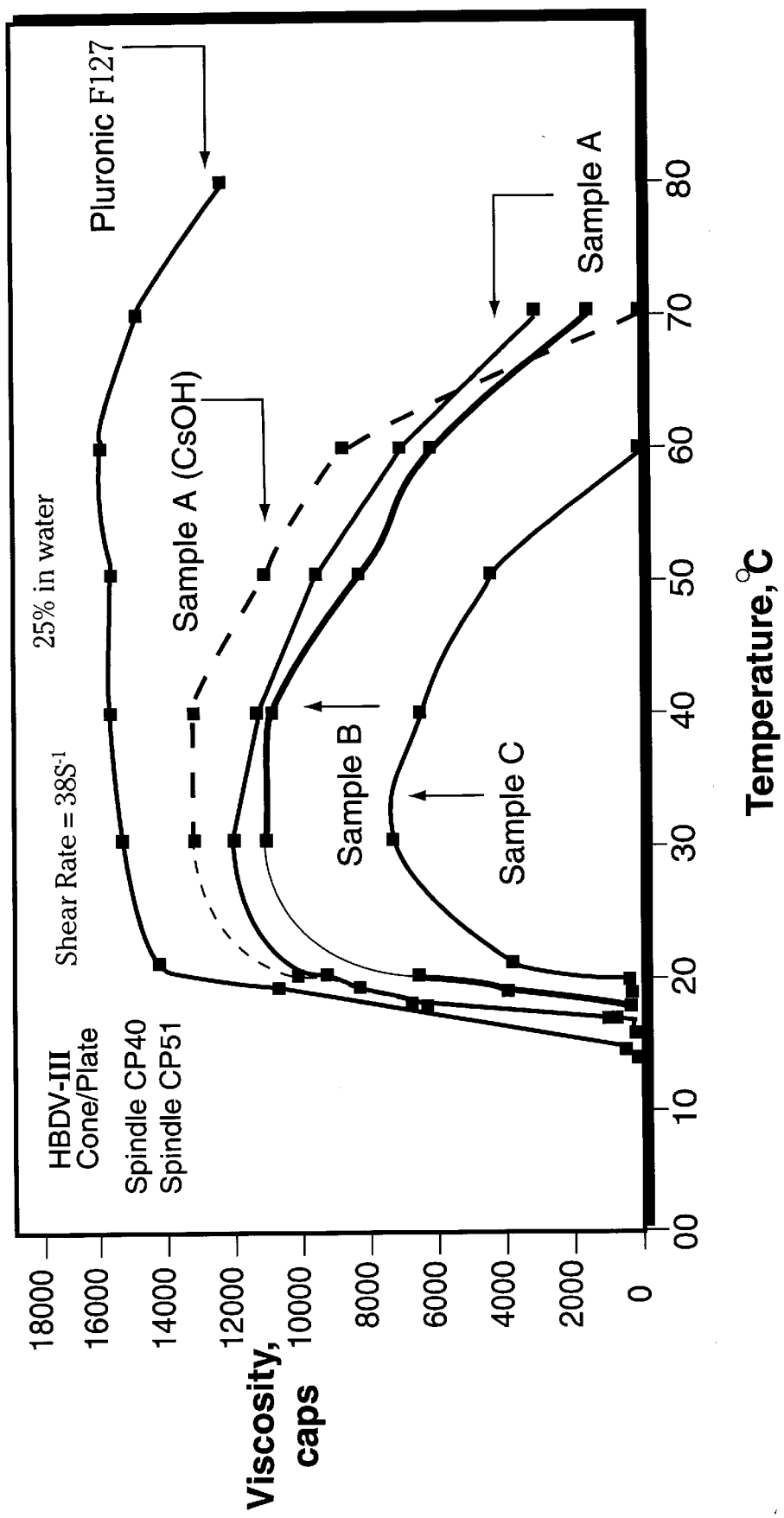

ORAL CARE COMPOSITIONS COMPRISING LIQUID POLYOXYALKYLENE COMPOUNDS AS SOLUBILIZERS/GELLING AGENTS

FIELD OF THE INVENTION

The present invention relates to oral care compositions comprising liquid polyoxyalkylene compounds (nonionic surfactants) suitable as additives with multifunctional benefits for aqueous oral care compositions. These copolymers exhibit utility as gelling agents for aqueous toothpaste formulations, as foam boosting additives for oral care formulations, and as solubilizers in mouthwash formulations.

BACKGROUND OF THE INVENTION

Polyoxyalkylene block copolymers have been used as non ionic surface active agents for many years. In general they have both hydrophobic and hydrophilic blocks which in combination give these compounds their surfactant properties. These products have been described before in numerous references. For example, Lunsted was the first to describe them in U.S. Pat. No. 2,674,619. Heterization of both the hydrophobic and hydrophilic blocks of nonionic block copolymer surfactants is well known in the art of surfactant chemistry. Lunsted, et.al. in U.S. Pat. No. 3,022,335, discloses surface active polyoxyalkylene compounds having plurality of heteric polyoxypropylene-polyoxyethylene chains, more specifically a heteric oxyalkylene-oxyethylene chain or chains as a hydrophobic nucleus to which oxyethylene chains were attached as the hydrophilic block. Patton, et. al., in U.S. Pat. No. 3,101,374, discloses surface active mixtures of polyoxyalkylene compounds composed of hydrophobic oxyalkylene chains or blocks which are condensed with a plurality of heteric oxyethylene-oxyalkylene chains. Patton also discloses that the resultant products were liquefied by addition of alkylene oxide, in a large enough percentage, to the heteric hydrophilic block. Otten & Schoene in U.S. Pat. No. 5,187,191, disclose an aqueous pesticide dispersion composed of a water insoluble pesticide, a liquid polyoxyalkylene compound having a plurality of heteric polyoxypropylene polyoxyethylene chains and water.

The aqueous gel properties and uses of solid polyalkylene/polyoxyethylene block polymers are well documented. U.S. Pat. No. 3,639,574 (Schmolka) assigned to BASF discloses polyoxyethylene/polyoxypropylene block copolymers as gelling agents for hydrogen peroxide compositions. In Lutz, U.S. Pat. No. 4,011,309, dentifrice compositions are disclosed which are composed of aqueous gel formulations that incorporate polyoxyethylene-polyoxypropylene block copolymers as the main gel component. Schmolka, in U.S. Pat. No. 4,343,785, discloses an aqueous gel dentifrice comprising polyoxybutylene-polyoxyethylene block copolymers. Schmolka also discloses mouthwash compositions which utilize polyoxybutylene-polyoxypropylene block copolymers as solubilizers.

Further, U.S. Pat. No. 3,740,421 (Schmolka) assigned to BASF discloses aqueous gels prepared using a triblock copolymer of polyoxyethylene/polyoxypropylene/polyoxyethylene suitable for pharmaceutical and personal care compositions at approximately 20–25% by weight. U.S. Pat. No. 4,465,663 (Schmolka) assigned to BASF discloses polyoxybutylene/polyoxyethylene block copolymers as gelling agents for aqueous gels useful in personal care and pharmaceutical applications. Some of these compounds are sold by the BASF Corporation under the PLURONIC® tradename.

Additionally, U.S. Pat. No. 4,272,394 and U.S. Pat. No. 4,411,810 disclose the use of polyoxyalkylene block copolymers in machine dishwashing applications. U.S. Pat. No. 4,925,988 discloses a nonionic surfactant employing a specific combination of alkanol, ethylene oxide and propylene oxide useful in an automatic dishwashing application. U.S. Pat. No. 5,374,368 describes the use of liquid EO/PO/EO triblock co-polymers (PLURONIC® L 31 and L 35 surfactants) in stable hydrogen peroxide releasing dental care compositions at levels of 55–90% by weight of the dental care composition. U.S. Pat. No. 3,867,533 discloses aqueous gel compositions containing solid EO/PO/EO triblock copolymers, having a molecular weight of 6,450–20,000 useful at levels of approximately 20% by weight. Said compositions are useful in preparing cosmetic formulations. U.S. Pat. No. 5,035,880 discloses a stable dentifrice compositions containing a cetylpyridinium bactericide and EO/PO/EO solid triblock copolymers (PLURONIC® F 127 surfactant), and polyethylene glycol at levels of 15–80% by weight. U.S. Pat. No. 4,476,107 discloses a mouthwash containing EO/BO (butylene oxide)/EO triblock copolymers at levels of 0.5–5.0% by weight. U.S. Pat. No. 5,057,307 discloses oral hygiene gels containing non-ionic surfactants, coating substances; and viscosifiers. Said non-ionic surfactants are PLURONIC® F 108 and F 127 surfactants available from BASF Corporation, Mt. Olive, N.J. U.S. Pat. No. 5,256,396 discloses a topical composition comprising an EO/PO/EO solid triblock copolymer (PLURONIC® F 127 surfactant) used at a level of more than 10% to about 17% by weight. EPO-546-627A discloses mouthwash compositions comprising solid EO/PO/EO triblock copolymers such as PLURONIC® L 108, F 88 surfactants at levels of 0.5–3% by weight. U.S. Pat. No. 5,073,368 discloses mouthwashes containing solid EO/PO/EO triblock copolymers such as PLURONIC® F 87 surfactant at levels of 0.1–3% by weight. WO 93/13750 discloses an ocular cleansing composition comprising solid PLURONIC® F 87 and paste PLURONIC® P 85 EO/PO/EO triblock copolymers. PLURONIC® P 85 surfactant is 4–9% by weight of the cleansing composition, PLURONIC® F 87 surfactant is 0.5–2% by weight of the cleansing composition. U.S. Pat. No. 5,096,698 discloses a dental creme composition containing a non-ionic triblock liquid EO/PO/EO copolymer or a solid triblock EO/PO/EO copolymer at levels of 0.1–5% by weight. Said copolymers help to prevent phase separation. PLURONIC® F 108 surfactant (solid) is most preferred, followed by PLURONIC® F 87, PLURONIC® F 127, and PLURONIC® L 72 surfactants. U.S. Pat. No. 4,272,394 discloses novel, low-foaming nonionic surfactant for machine dishwashing compositions. U.S. Pat. No. 4,411,810 discloses a low foaming, low cloud point, nonionic surfactant for machine dishwashing compositions. Finally, JP 47-48366 B4 discloses a process for producing tasteless, liquid, heteric polyoxyalkylene compounds of molecular weight 1000 or higher. U.S. Pat. No. 5,187,191 discloses polyoxyalkylene block copolymers in agricultural formulations. U.S. Pat. No. 5,496,542, U.S. Pat. No. 5,374,368, and U.S. Pat. No. 5,424,060 disclose the use of a polyoxyalkylene compound for formulating a stable percarbonate formulation as well as a dentifrice composition.

Clearly, it is known to those ordinarily skilled in the art that solid block copolymers of ethylene oxide and propylene oxide are useful in aqueous dentifrice compositions. However, a typical disadvantage with the solid block copolymers is their physical form. Triblock copolymers of ethylene oxide and propylene oxide, wherein the ethylene oxide content in the copolymer is over 70%, are typically solids above a MW of 3000. Solid, triblock copolymers of ethylene oxide and propylene oxide can pose handling problems during the manufacture of aqueous dentifrice compositions. Such difficulties typically arise due to their high melting points. In many cases, the solid triblock copolymers have to be converted to their molten state during processing.

The Applicants have surprisingly discovered that when the solid triblock copolymers are rendered liquid via a carefully controlled addition of a heteric mixture of ethylene oxide and propylene oxide to the hydrophobic propyleneoxide block, the resulting product essentially retains the properties of the solid block copolymer and has the benefit of ease of handling in formulating personal care formulations. Specifically, the Applicants' invention overcomes the problems in the art by preparing a liquid copolymer useful in aqueous oral care compositions while essentially retaining the properties of the solid block copolymer. Thus the liquid copolymer of the invention affords ready solubility in aqueous oral care compositions, increased ease of handling and pumping, and utility as gelling or solubilizing agents for such compositions.

Additionally, the references listed hereinabove describe methods of preparation for many different polyoxyalkylene polyether surfactants. However, an undesirably broad distribution of molecular weights is obtained both in the hydrophobe and hydrophile portion of the polymer. The broad distribution of molecular weight products, which result from the anionic living polymerization, may be narrowed to some extent by reduction of a side reaction which develops during propylene oxide additions. Some of the side reactions may result in terminal unsaturation. Cuscurida in U.S. Pat. No. 3,393,243, discloses a method for preparation of propylene oxide based polyether polyols with reduced content of terminal unsaturation by using CsOH as a catalyst. Ott in U.S. Pat. No. 4,764,567, discloses a method of preparation for narrow molecular weight distribution products by using CsOH during the ethylene oxide addition. Finally, Otten in U.S. Pat. No. 4,902,834, discloses an improved process for the preparation of capped polyoxyalkylene block polyethers using CsOH.

Further, the Applicants have also discovered that the use of cesium hydroxide as a catalyst in the synthesis of the liquid polyoxyalkylene block copolymers of the present invention resulted in further improvement in the gel characteristics of the liquid polymer relative to a potassium hydroxide catalyzed material.

SUMMARY OF THE INVENTION

An oral care composition comprising 0.1–50% of the liquid polyoxyalkylene compound having the formula:

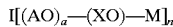

wherein
I is a initiator or a mixture of initiators having at least one substituent selected from the group including but not limited to —OH, or —NH2;
AO is a $C_{3-4}$ alkylene oxide or mixtures of $C_{3-4}$ alkylene oxide arranged in a block sequence;
XO is (EO)hd b(AO)$_c$ wherein EO is ethylene oxide and EO and AO are distributed randomly;
M is hydrogen or alkali metal or alkaline earth metal; and
a is an integer from about 15–35,
b is an integer from about 50–150, c is an integer from about 7–90,
n is an integer from 1–3;
Preferred MWs are from 8000–28000, more preferred 9000–24000, most preferred 10500–19500.

DETAILED DESCRIPTION

An oral care comprising 0.1–50% of the liquid polyoxyalkylene compound having the formula:

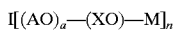

wherein
I is a initiator or a mixture of initiators having at least one substituent selected from the group including but not limited to —OH, or —NH2;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly;
M is hydrogen or alkali metal or alkaline earth metal; and
a is an integer from about 15–35, more preferably 20–32, most preferably 24–31,
b is an integer from about 50–150, more preferably 65–135, most preferably 70–120,
c is an integer from about 7–90, more preferably 10–70, most preferably 15–45,
n is an integer from 1–3, more preferably 2–3, most preferably 2;
The initiator is selected from the group consisting of propylene glycol, dipropylene glycol, ethylene glycol, and diethylene glycol, and glycerol, most preferably the initiator is propylene glycol.
Preferred MWs are from about 8000–28000, more preferred about 9000–24000, most preferred about 10500–19500.
Triblock copolymers of EO and PO (EO/PO/EO) are excluded from the scope of this invention.

The Preparation of the Polyoxyalkylene Copolymers of the Present Invention

All polyoxyalkylene block copolymers of the present invention were prepared by conventional techniques in 1 or 2 gallon stainless steel autoclaves that were equipped with stirring, pressure gauge, thermocouple and addition tube. For instance, an initiator, in this case propylene glycol, and catalyst, selected from the group including but not limited to NaOH, KOH, CsOH, were vacuum stripped in a stainless steel stirred autoclave at 120° C. to remove water. Formation of the polyoxypropylene block was achieved by the addition of propylene oxide at 105° C. under a nitrogen atmosphere with addition rates set such that the overall pressure does not exceed 90 psig and the residual PO concentration at the end of addition does not exceed 18%. To the polyoxypropylene block was added a mixture of ethylene oxide and propylene oxide to form a mixed oxide hydrophilic block. Mixed oxide additions were carried out at 135° C. with the same pressure constraints as above. Other products produced with polyoxyethylene hydrophilic blocks used an ethylene oxide addition temperatures of 135° C. The catalyst content for these syntheses was between 0.06%–0.50% final catalyst level. The ethylene oxide and mixed oxide charges were added under a 34 psig nitrogen pad with addition rates to keep the vapor phase EO concentration below the safe explosive limit which can be calculated according to Siwek in Siwek, R., Rozenberg, E., "Ethylene Oxide Vapor Decomposition—Process and Protective Measures" Zeitschrift fur die fett-, Ol-,Tensid-,Kosmetik-undPharmaindustrie, Vol 115, Augsburg, Sep. 1, 1989, NR14-1.

The final products were neutralized by addition of 85% phosphoric acid and inhibited by addition of 100 ppm t-butylhydroxytoluene.

BRIEF DESCRIPTION OF THE DRAWING

The Utility of the Liquid Polyoxyalkylene Copolymers of the Present Invention The aqueous gel profiles of the liquid polyoxyalkylene block copolymers of this invention were compared with a aqueous gel prepared with a conventional solid triblock copolymer and the results are shown in FIG. 1. The solid, triblock copolymer used as a comparative example in this study, is poloxamer 407 available from BASF, Mt. Olive, N.J. under the tradename PLURONIC® F127 surfactant. The aqueous gels were prepared by mixing the polyethers with water and storing the solutions at about 5° C. for a period of 24 hours. At the end of 24 hours, the solutions were clear and upon warming to ambient temperatures produced a sparkling clear, ringing gel. The viscosity profiles of the gels were measured using a Brookfield HBDV-III viscometer using spindles CP40 and CP51. FIG. 1 shows that the gel profiles of the liquid polyethers on this invention are essentially similar to those observed with Poloxamer 407. Furthermore, surprisingly the lower transition temperature for the liquid polyethers of this invention are very nearly similar to that observed with Poloxamer 407. The similarities in the lower transition temperatures allows the liquid polyethers of this invention to be used in oral care formulations in the same way as the solid, triblock copolymers. In FIG. 1, Sample A (CsOH catalyzed) shows a significant improvement over Sample A which was catalyzed with KOH.

TABLE 1

PHYSICAL PROPERTIES OF THE PRESENT INVENTION
COMPARED TO A PRIOR ART COMPOUND (POLOXAMER 407)

| Sample | Pour Point/(Melt Point) °F. | Form |
|---|---|---|
| A | 68 | liquid |
| A(CsOH) | 65 | liquid |
| B | 50 | liquid |
| C | 36 | liquid |
| Poloxamer 407 | 140 | solid |

Poloxamer 407 is a triblock copolymer of EO and PO with the following ideal structure as defined in the Official Monograph NF 18 for poloxamer block copolymers:

$$HO(C_2H_4O)_{101}(C_3H_6O)_{56}(C_2H_4O)_{101}H$$

Sample A of the present invention has the ideal polymer structure represented by:

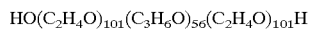

Sample B of the present invention has the polymer structure

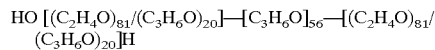

Sample C of the present invention has the polymer structure

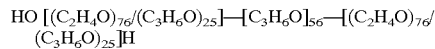

All samples are catalyzed by KOH unless otherwise indicated

Utility of the Liquid Polyoxyalkylene Copolymers of the Present Invention in Oral Care Compositions Aqueous oral care compositions comprising the liquid copolymers of the present invention preferably contain about 0.1–50% of the liquid copolymer by weight of the composition; more preferably about 0.5–25%; most preferably about 1–20%.

Typical aqueous based dentrifice compositions comprising the liquid copolymer of the invention may further contain other ingredients such as surfactants selected from anionic surfactants such as sodium lauryl sulfate, sodium N-lauryl sarcosinate, sodium lauryl sulfoacetate, and sodium alkyl glyceryl ether sulfonate. Additionally, the dentrifice formulation may also include abrasives such as hydrated silica, dicalciumphosphate dihydrate, calcium carbonate, sodium bicarbonate, calcium pyrophosphate and alumina. Furthermore, the dentrifice composition can also contain humectants such as, glycerin, sorbitol, propylene glycol, xylitol and liquid polyethylene glycols. Thickening agents such as sodium carboxymethyl cellulose, cellulose ethers, xanthan gum, carageenans, sodium alginate, carbopols can also be included in the dentrifice composition. Inorganic thickeners such as silica thickeners, sodium aluminum silicates and clays can also be used to provide appropriate rheology. Also other ingredients such as tartar control agents such as tetrasodium pyrophosphate, GANTREZ polymer® S-70, sodium tripolyphosphate, and zinc citrate can be included. Dentrifice compositions may also contain peroxygen compounds selected from but not limited to hydrogen peroxide and inorganic peroxides. Dentrifice actives such as triclosan, sodium monofluorophosphate, sodium fluoride, anti-plaque agents, anti-caries agents, anti-inflammatory agents can also be included in the composition. Aesthetic ingredients such as flavoring agents, such as peppermint, spearmint oils, opacifying agents, sweeteners can also be included in small amounts in the dentrifice composition.

Typical aqueous based mouthwash formulations comprising the liquid copolymer of this invention may also contain other ingredients such as alcohol, preferably ethanol to enhance the solubility of flavoring oils and other organic compounds which have low or limited solubility in water. A few glycol compounds can also be used in combination with or in place of alcohol, such as glycerin, sorbitol or propylene glycol. Anti-bacterial, anti-microbial, plaque-penetrating agents also constitute essential components of a mouthwash formulation. Essential oils including, but not limited to, such as clove oil, cinnamon oil, peppermint oil, spearmint oil are also be a part of the mouthwash formulation. Anti-germicidal compounds such as the quarternary ammonium compounds also find utility in mouthwash compositions. Other aesthetic ingredients such as dyes and sweetening agents can also re incorporated into the mouthwash formulation.

The solubilization properties of the liquid polyoxyalkylene compounds of this invention were compared to conventional block copolymers solubilizers such as a solid, poloxamer 407. These are shown in Table 2. Three common flavor oils typically employed in mouthwash compositions, were selected in this study. These are cinnamon oil, peppermint oil and clove oil. In each test, 0.1% aqueous solution of the flavor oil was prepared with each flavor oil composition, the prepared solutions were hazy or cloudy in the absence of the compounds of the present invention. All additives were added at a fixed concentration of 1.5%. Table-2 shows that with cinnamon oil all three liquid polyoxyalkylene compounds of this invention were able to solubilize the flavor oil to produce a clear composition and performed similar to the control with peppermint oil. Samples A & B gave hazy compositions similar to the control. However, Sample C of the invention gave a clear composition. All three liquid polyethers of this invention gave clear compositions with clove oil and performed similar to control.

TABLE 2

SOLUBILIZATION PROPERTIES OF THE LIQUID POLYOXYALKYLENE COMPOUNDS OF THE PRESENT INVENTION.

| # | FLAVOR OIL | % ADDITIVE | APPEARANCE |
|---|---|---|---|
| 1 | 0.1% Cinnamon Oil | None | Hazy |
| | | 1.5% Poloxamer 407 (control) | Clear |
| | | 1.5% Sample A | Clear |
| | | 1.5% Sample B | Clear |
| | | 1.5% Sample C | Clear |
| 2 | 0.1% Peppermint Oil | None | Hazy |
| | | 1.5% Poloxamer 407 (control) | Hazy |
| | | 1.5% Sample A | Hazy |
| | | 1.5% Sample B | Hazy |
| | | 1.5% Sample C | Clear |
| 3 | 0.1% Clove Oil | None | Hazy |
| | | 1.5% Poloxamer 407 (control) | Clear |
| | | 1.5% Sample A | Clear |
| | | 1.5% Sample B | Clear |
| | | 1.5% Sample C | Clear |

The following non-limiting examples serve to illustrate the utility of the present invention. All percentages are weight percent of the total composition.

EXAMPLE 1

A Toothpaste Formulation 0.05–0.2% actives selected from group including, but not limited to, sodium fluoride, stannous fluoride, sodium monoflurophosphate;

10–55% humectants, selected from the group including, but not limited to, glycerin, sorbitol, propylene glycol, and polyalkylene glycol;

0.1–50% liquid polyoxyalkylene compound of the invention wherein:

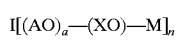

wherein
I is a initiator or a mixture of initiators having at least two carbon atoms wherein at least one carbon atom must have the substituent selected from the group including but not limited to —OH, or —NH2;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly;
M is hydrogen or alkali metal or alkaline earth metal; and
a is an integer from about 15–35,
b is an integer from about 50–150,
c is an integer from about 7–90,
n is an integer from 1–3;
10–50% water;
10–55% abrasives, selected from the group including, but not limited to, calcium pyrophospate, dicalcium phosphate, hydrated silica
2–10% binders, including, but not limited to, gum karaya, tragacanth USP, sodium alginate; Irish moss and methyl cellulose;
2–8% surfactants, including, but not limited to, sodium lauryl sulfate, sodium N-lauryl sarcosinate, dioctyl sodium sulfosuccinate, sodium lauryl sulfoacetate;
0–10% Peroxygen compounds selected from but not limited to hydrogen peroxide and inorganic peroxides.

EXAMPLE 2

A Mouthwash Formulation 0.01–0.1% anti-bacterial agents including, but not limited to, such as phenolic compounds, beta-napthol, thymol, chlorothymol, hexylresorcinol 5–25% humectants, including, but not limited to, glycerol, sorbitol, propylene glycol, and polyalkylene glycol 0.01–0.2 essential oils, including, including, but not limited to, clove oil, peppermint oil, spearmint oil 0–30% ethyl alcohol 0.1–5% the liquid polyoxyalkylene compound of the invention wherein:

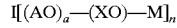

wherein
I is a initiator or a mixture of initiators having at least two carbon atoms wherein at least one carbon atom must have the substituent selected from the group including but not limited to —OH, or —NH2;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly
M is hydrogen or alkali metal or alkaline earth metal; and
a is an integer from about 15–35,
b is an integer from about 50–150,
c is an integer from about 7–90,
n is an integer from 1–3;
40–80% Water

What is claimed is:

1. An aqueous oral care composition comprising 0.1–50% of a liquid polyoxyalkylene compound of the formula:

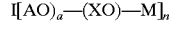

wherein:
I is an initiator or a mixture of initiator shaving at least two carbon atoms, wherein at least one carbon atom must have a substituent selected from —OH or —NH$_2$;
AO is a $C_{3-4}$ alkylene oxide or mixtures of $C_{3-4}$ alkylene oxide arranged in a block sequence;

XO is $(EO)_b(AO)_c$ wherein EO is ethylene oxide and EO and AO are distributed randomly;

M is hydrogen or alkali metal or alkaline earth metal;

a is an integer from about 15–35;

b is an integer from about 50–150;

c is an integer from about 7–90; and n is an integer from 1–3.

2. An aqueous oral care composition according to claim 1, wherein a is 20–32, b is 65–135, c is 10–70, and n is 2–3.

3. An aqueous oral care composition according to claim 1, wherein a is 24–31, b is 70–120, c is 15–45, and n is 2.

4. A toothpaste composition comprising:

0.05–0.2% active selected from sodium fluoride, stannous fluoride and sodium monoflurophosphate;

10–55% humectant selected from glycerin, sorbitol, propylene glycol and polyalkylene glycol;

0.1–50% liquid polyoxyalkylene compound of the formula:

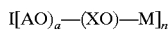

$$I[AO]_a\text{—}(XO)\text{—}M]_n$$

wherein:

I is an initiator or a mixture of initiator shaving at least two carbon atoms, wherein at least one carbon atom must have a substituent selected from —OH or —NH$_2$;

AO is a C$_{3-4}$ alkylene oxide or mixtures of C$_{3-4}$ alkylene oxide arranged in a block sequence;

XO is $(EO)_b(AO)_c$ wherein EO is ethylene oxide and EO and AO are distributed randomly;

M is hydrogen or alkali metal or alkaline earth metal;

a is an integer from about 15–35;

b is an integer from about 50–150;

c is an integer from about 7–90; and n is an integer from 1–3;

10–50% water;

10–55% abrasive selected from calcium pyrophosphate, dicalcium phosphate, hydrated silica;

2–10% binder selected from gum karaya, tragacanth USP, sodium alginate, Irish moss and methyl cellulose;

2–8% surfactant selected from sodium lauryl sulfate, sodium N-lauryl sarcosinate, dioctyl sodium sulfosuccinate and sodium lauryl sulfoacetate; and 0–10% peroxygen compound selected from hydrogen peroxide and inorganic peroxides.

5. A mouthwash composition comprising:

0.01–0.1% anti-bacterial agent selected from phenolic compounds, beta-napthol, thymol, chlorothymol and hexylresorcinol;

5–25% humectant selected from glycerol, sorbitol, propylene glycol and polyalkylene glycol;

0.01–0.2% essential oil selected from clove oil, peppermint oil and spearmint oil;

0–30% ethyl alcohol;

0.1–5% liquid polyoxalkylene compound of the formula:

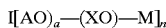

$$I[AO]_a\text{—}(XO)\text{—}M]_n$$

wherein:

I is an initiator or a mixture of initiator shaving at least two carbon atoms, wherein at least one carbon atom must have a substituent selected from —OH or —NH$_2$;

AO is a C$_{3-4}$ alkylene oxide or mixtures of C$_{3-4}$ alkylene oxide arranged in a block sequence;

XO is $(EO)_b(AO)_c$ wherein EO is ethylene oxide and EO and AO are distributed randomly;

M is hydrogen or alkali metal or alkaline earth metal;

a is an integer from about 15–35;

b is an integer from about 50–150;

c is an integer from about 7–90; and n is an integer from 1–3;

40–80% water.

* * * * *